United States Patent
Lee et al.

(10) Patent No.: US 8,850,602 B2
(45) Date of Patent: Sep. 30, 2014

(54) METHOD FOR PROTECTING APPLICATION AND METHOD FOR EXECUTING APPLICATION USING THE SAME

(75) Inventors: Min-cheol Lee, Seoul (KR); Jae-won Choi, Seoul (KR); Dong-sung Kim, Anyang-si (KR); Jong-shin Kim, Seoul (KR); Nam-geol Lee, Seoul (KR)

(73) Assignee: Samsung Electronics Co., Ltd (KR)

( * ) Notice: Subject to any disclaimer, the term of this patent is extended or adjusted under 35 U.S.C. 154(b) by 85 days.

(21) Appl. No.: 13/512,527

(22) PCT Filed: Nov. 25, 2010

(86) PCT No.: PCT/KR2010/008410
§ 371 (c)(1),
(2), (4) Date: May 29, 2012

(87) PCT Pub. No.: WO2011/065768
PCT Pub. Date: Jun. 3, 2011

(65) Prior Publication Data
US 2012/0311720 A1   Dec. 6, 2012

(30) Foreign Application Priority Data

Nov. 27, 2009 (KR) .......... 10-2009-0116073

(51) Int. Cl.
*G06F 21/00* (2013.01)
*H04L 9/08* (2006.01)
*G06F 21/12* (2013.01)

(52) U.S. Cl.
CPC .......... *G06F 21/121* (2013.01); *H04L 2209/56* (2013.01); *H04L 9/0866* (2013.01); *H04L 2209/603* (2013.01)
USPC ............................................ 726/27; 713/189

(58) Field of Classification Search
CPC ... G06F 21/121; H04L 9/0866; H04L 9/0863; H04L 2209/60; H04L 2209/56
See application file for complete search history.

(56) References Cited

U.S. PATENT DOCUMENTS

| | | | | |
|---|---|---|---|---|
| 5,438,622 | A * | 8/1995 | Normile et al. | 380/46 |
| 5,636,279 | A * | 6/1997 | Katta et al. | 380/217 |
| 7,095,855 | B1 * | 8/2006 | Collins | 380/241 |
| 8,050,405 | B2 * | 11/2011 | Camp et al. | 380/260 |
| 8,572,684 | B1 * | 10/2013 | Sama | 726/2 |

(Continued)

FOREIGN PATENT DOCUMENTS

| | | |
|---|---|---|
| KR | 1020050000824 | 1/2005 |
| KR | 1020090058184 | 6/2009 |

OTHER PUBLICATIONS

Dierks, T. et al., The TLS Protocol Version 1.0, Jan. 1999, Copyright (C) The Internet Society (1999), 72 pages.
Australian Examination Report dated Aug. 11, 2014 issued in counterpart Application No. 2010325337.

*Primary Examiner* — Michael R Vaughan
(74) *Attorney, Agent, or Firm* — The Farrell Law Firm, P.C.

(57) ABSTRACT

An application protection method and an application execution method using the same are provided. The application protection method generates a key needed to execute the application which is provided to a user terminal using information on the user terminal, information on the application, and a part of text; and transmits the generated key to the user terminal. Therefore, the application is executed on the device which has a legal right for the application, thereby preventing the illegal use of the application.

15 Claims, 4 Drawing Sheets

(56) References Cited

U.S. PATENT DOCUMENTS

| | | | |
|---|---|---|---|
| 2005/0021992 A1* | 1/2005 | Aida et al. | 713/200 |
| 2007/0033418 A1* | 2/2007 | Okawa | 713/192 |
| 2009/0060185 A1* | 3/2009 | Tresser | 380/255 |
| 2010/0246811 A1* | 9/2010 | Sadler | 380/28 |
| 2010/0250968 A1* | 9/2010 | Sadler | 713/193 |

* cited by examiner

Fig. 5

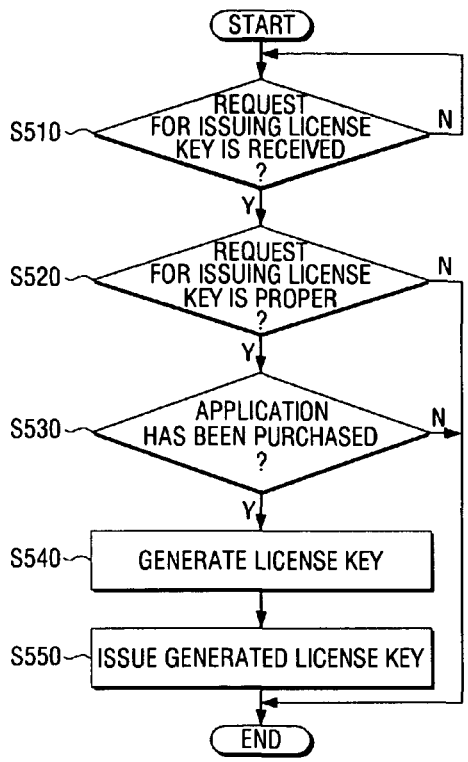

Fig. 6

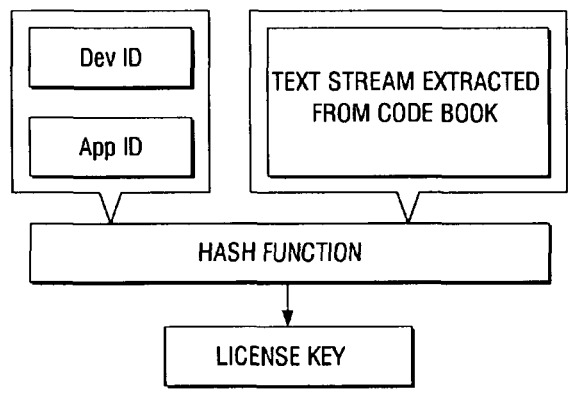

Fig. 7

History is the study of the human past, with special attention to the written record. Scholars who write about history are called historians. It is a field of research which uses a narrative to examine and analyse the sequence of events, and it often attempts to investigate objectively the patterns of cause and effect that determine events. Historians debate the nature of history and the lessons history teaches. A famous quote by the philosopher George Santayana has it that "Those who cannot remember the past are condemned to repeat it." The stories common to a particular culture, but not supported by external sources (such as the legends surrounding King Arthur) are usually classified as cultural heritage rather than the "disinterested investigation" needed by the discipline of history.

METHOD FOR PROTECTING APPLICATION AND METHOD FOR EXECUTING APPLICATION USING THE SAME

PRIORITY

This application is a National Phase Entry of PCT International Application No. PCT/KR2010/008410, which was filed Nov. 25, 2010, and claims priority to Korean Patent Application No. 10-2009-0116073, which was filed in the Korean Intellectual Property Office, on Nov. 27, 2009, the content of each of which is incorporated herein by reference.

BACKGROUND OF THE INVENTION

1. Field of the Invention

The present invention relates generally to a method for protecting an application, and more particularly, to an application protection method to prevent an unauthorized user from copying and using the application.

2. Description of the Related Art

A software application is protected by intellectual property rights, since it is a creation of the mind of a programmer. However, illegal downloading and sharing of applications are prevalent and there are insufficient protection means against them.

Therefore, there is a need for methods, which enhance protection of applications which are programmers' assets, as part of an effort to prevent a decline in application innovation as well as pecuniary loss caused by illegal use of applications.

SUMMARY OF THE INVENTION

Accordingly, the present invention has been made to solve the above-stated problems occurring in the prior art, and provides an application protection method which allows an application to be executed only in the device which has purchased the application or the device which has a legal right and an application execution method using the same.

According to an aspect of the present invention, there is provided an application protection method, which includes providing a user terminal with an application, generating a key needed to execute the application using information on the user terminal, information on the application, and a part of text, and transmitting the generated key to the user terminal.

According to another aspect of the present invention, there is provided an application execution method, which includes determining whether a key which is generated to execute the application using information on the user terminal, information on the application, and a part of text is valid or not, and executing the application if it is determined that the key is valid.

BRIEF DESCRIPTION OF THE DRAWINGS

The above and/or other aspects, features and advantages of the present invention will be more apparent from the following detailed description taken in conjunction with the accompanying drawings, in which:

FIG. 5 is a flowchart illustrating the process that a DRM server issues a license key to a DRM client according to an embodiment of the present invention;

FIG. 6 is a diagram illustrating a method for generating a license key according to an embodiment of the present invention; and FIG. 7 is a diagram illustrating a method for generating a text stream according to an embodiment of the present invention.

DETAILED DESCRIPTION OF THE EMBODIMENTS OF THE PRESENT INVENTION

Figure 1:
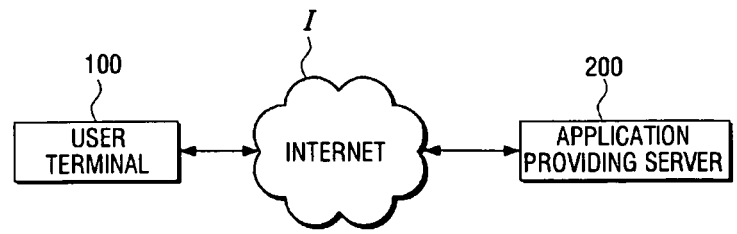
FIG. 1 is a block diagram illustrating an application providing system according to an embodiment of the present invention.

Various embodiments of the present invention will be described in detail with reference to the accompanying drawings. In the following description, the same reference numerals are used for the same elements throughout the drawings to refer to the same or similar elements. Detailed construction and elements are provided to assist in a comprehensive understanding of the invention. Thus, it is apparent to those of ordinary skill in the art that the present invention may be embodied in various forms and should not be construed as limited to the embodiments described herein. Detailed descriptions of well-known functions and structures are omitted to avoid obscuring the subject matter of the present invention with unnecessary detail.

FIG. 1 is a block diagram illustrating an application providing system according to an embodiment of the present invention. Referring to FIG. 1, the application providing system is built in such a manner that a user terminal 100 is connected to an application providing server 200 via Internet I to communicate with each other.

The application providing server 200 operates a web page to provide application on Internet I, and sells application to the user terminal 100 which accesses the web page. That is, the application providing server 200 provides applications by transmitting applications to the user terminal 10 that has purchased the applications.

The application providing server 200 issues a license key to the user terminal 100. The license key is necessary to execute the application. That is, if the user terminal 100 does not have a valid license key, the user terminal 100 may not execute the installed application.

The user terminal 100, which is owned by a user, receives the application that the user purchases from the application providing server 200, installs the application, and executes the installed application.

To execute the application, the user terminal 100 needs to have a valid license key. If the user terminal 100 does not have a license key, or if the user terminal 100 possesses an invalid license key, the user terminal 100 may not execute application.

Figure 2:
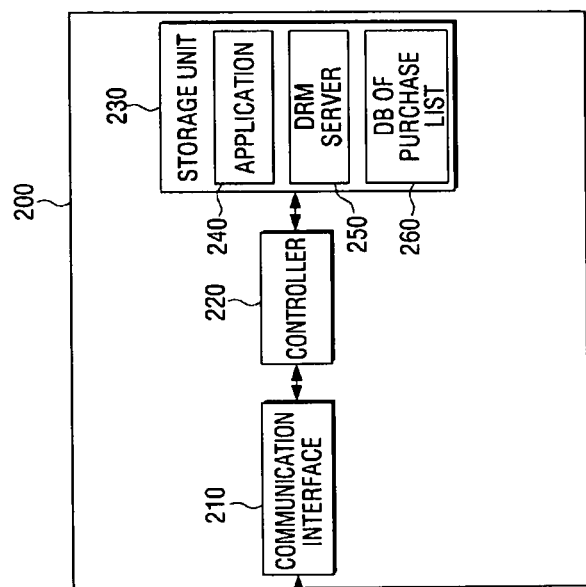
FIG. 2 is a block diagram illustrating a user terminal and an application providing server which constitute the application providing system of FIG. 1.
Figure 2:
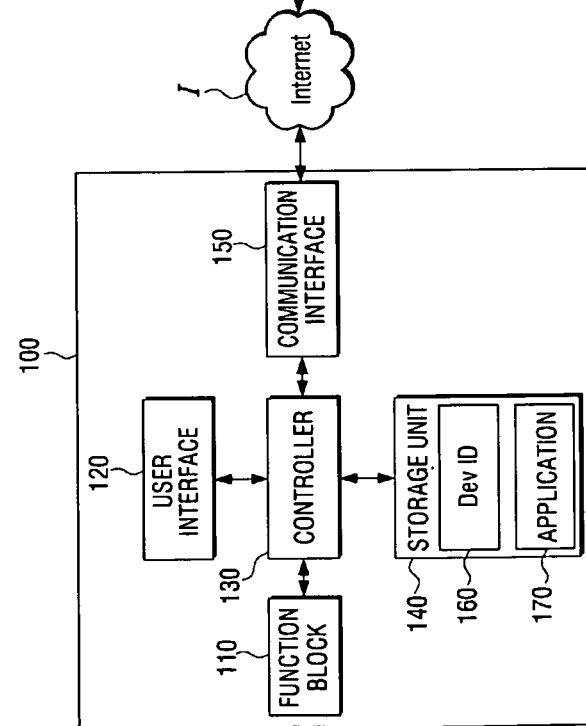

FIG. 2 is a block diagram illustrating the user terminal 100 and the application providing server 200 which constitute the application providing system of FIG. 1.

Referring to FIG. 2, the user terminal 100 includes a function block 110, a user interface 120, a controller 130, a storage unit 140, and a communication interface 150.

The function block 110 performs essential functions of the user terminal 100. If the user terminal 100 is a mobile phone, the function block 110 performs mobile telecommunications such as mobile telephone or text messaging, if the user terminal 100 is an MPEG layer 3 (MP3) player, the function block 110 plays back audio content, and if the user terminal 100 is a TeleVision (TV), the function block 100 receives and plays a broadcasting program.

The user interface 120 operates as an output means to output the result of the operation performed by the function block 110 and an input means for receiving a command from a user.

The storage unit 140 provides a storage space in which Device Identification (Dev ID) 160 and application 170 are stored. The Dev ID 160 is information which indicates the user terminal 100, and the application 170 is purchased and thus transmitted from the application providing server 200.

The communication interface 150 sets and keeps connection with the application providing server 200 to communicate with each other.

The controller 130 controls the function block 110 according to a command input by a user using the user interface 120. If a command to execute the application 170 is input by a user through the user interface 120, the controller 130 executes the installed application 170. The process that the controller 130 executes the application will be explained later in detail with reference to FIG. 4.

As illustrated in FIG. 2, the application providing server 200 comprises a communication interface 210, a controller 220, and a storage unit 230.

The communication interface 210 sets and keeps connection with the user terminal 100 to communicate with each other.

The storage unit 230 stores application 240 to be sold to the user terminal 100, a The (Digital Rights Management) (DRM) server 250 is a program providing DRM for applications, and issues a license key required to execute the applications. The Data Base (DB) 260 stores the list of applications 240 that the user terminal 100 has purchased.

The controller 220 retrieves the application which a user has purchased using the user terminal 100 from the storage unit 230, and transmits the retrieved application to the user terminal 100 through the communication interface 210. The controller 220 stores the list of applications that the user terminal 100 has purchased in the DB 260 of purchase list.

The controller 220 executes the DRM server 250 stored in the storage unit 230, and manages DRM for the application which has been purchased.

To provide DRM for the purchased application, the DRM server 250 is connected to a DRM client (not shown) of the application 170 installed on the user terminal 100 to communicate with each other, and operates in association with the DRM client.

Figure 3:
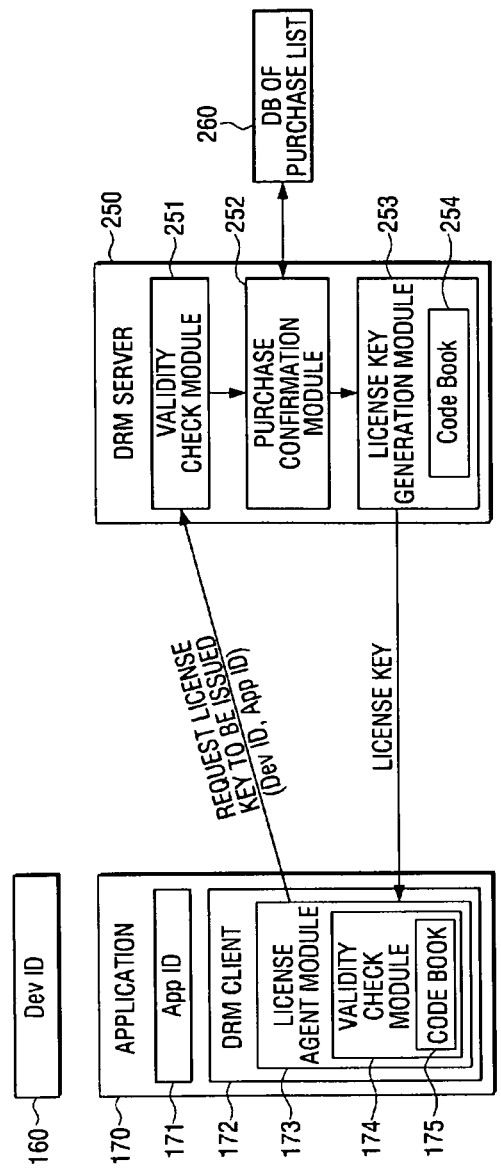
FIG. 3 is a diagram illustrating the detailed structure of application and a DRM server according to an embodiment of the present invention.

The structure of the application 170 installed on the user terminal 100 and the structure of the DRM server 250 installed on the application providing server 200 is explained with reference to FIG. 3. FIG. 3 is a diagram illustrating the detailed structure of the application 170 and the DRM server 250 according to an embodiment of the present invention.

Referring to FIG. 3, the application 170 installed on the user terminal 100 comprises Application Identification (App ID) 171 and a DRM client 172. The DRM client 172 is packed in the application 170.

The App ID 171 specifies the application 170. The DRM client 172 is a program which is executed on the user terminal 100 to provide DRM for the application 170, and operates as a client of the DRM server 250.

The DRM client 172 comprises a license agent module 173, the license agent module 173 comprises a validity check module 174, and the validity check module 174 comprises a code book 175.

The license agent module 173 determines whether a license key exists in the storage unit 140 of the user terminal 100 or not. If it is needed to issue a license key, the license agent module 173 requests the DRM server 250 to issue a license key.

The validity check module 174 checks the validity of the license key existing in the storage unit 140, and transmits the checked result to the license agent module 173. When checking the validity of a license key, the validity check module 174 refers to the code book 175.

The code book 175 is the type of a text file. The texts contained in the code book 175 are identical to those of a code book 254 included in the DRM server 250 which will be explained later.

The DRM server 250 is a program which is executed so that the application providing server 200 provides DRM for the application 170, and operates as a server of the DRM client 172. The DRM server 250 comprises a validity check module 251, a purchase confirmation module 252, and a license key generation module 253.

The validity check module 251 determines whether the request for issuing a license key received from the user terminal 100 is valid. That is, the validity check module 251 determines if a right DRM client 172 requests that a license key be issued.

The purchase confirmation module 252 determines whether the user terminal 100 on which the application 170 is installed is a right terminal which has purchased the application 170. To do so, the purchase confirmation module 252 refers to the DB of purchase list 260.

The license key generation module 253 generates a license key, and transmits the generated license key to the license agent module 173. When generating a license key, the license key generation module 253 refers to the code book 254.

The texts contained in the code book 254 are identical to those of the code book 175 included in the DRM client 172 described above.

The method that the license key generation module 253 generates a license key will be explained later in detail with reference to FIG. 6.

The restriction process where the DRM client 172 packed in the application 170 restricts the user terminal 100 to executing the application 170 according to whether the user terminal 100 has a valid license key is described with reference to FIG. 4.

The application 170 purchased from the application providing server 200 is installed on the user terminal 100.

Figure 4:
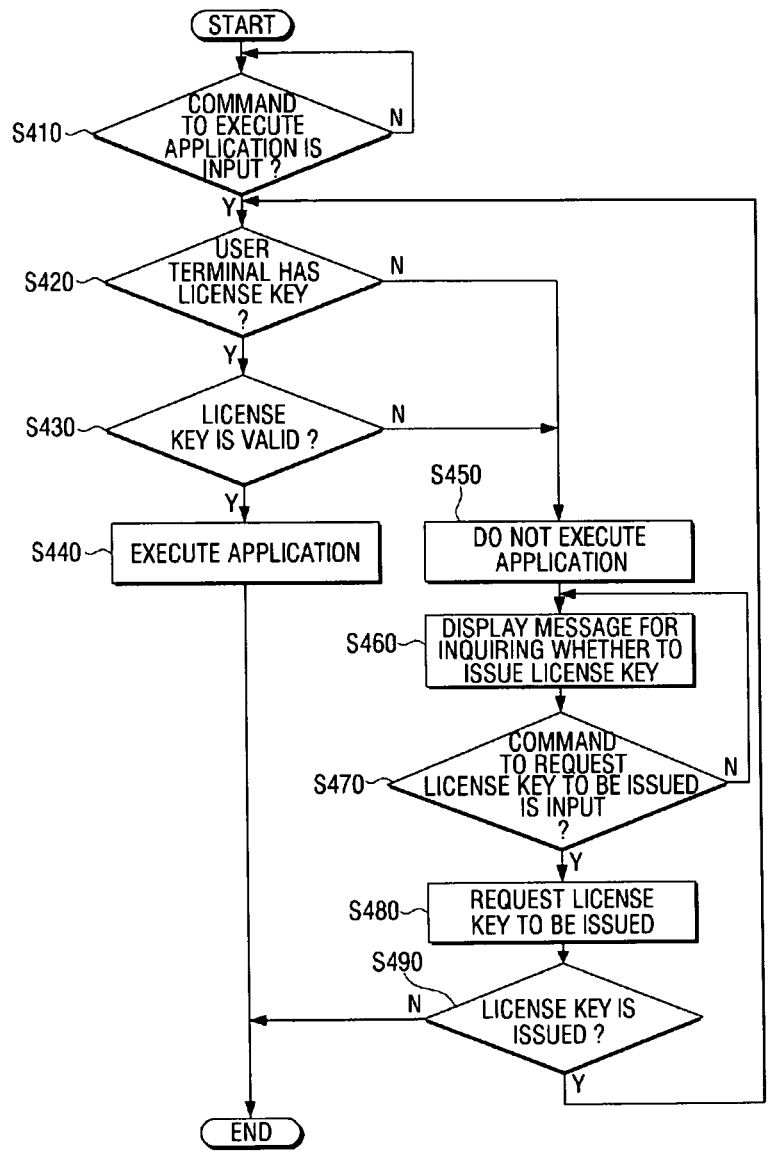
FIG. 4 is a flowchart illustrating the process that a DRM client restricts a user terminal to executing application according to an embodiment of the present invention.

As illustrated in FIG. 4, if a user inputs a command to execute the application 170 in Step 410, the license agent module 173 of the DRM client 172 executed by the controller 130 determines whether or not the user terminal 100 has a license key in Step 420. The determination in Step 420 is performed by the process wherein the license agent module 173 determines whether or not a license key is stored in the storage unit 140 of the user terminal 100.

If it is determined that the user terminal 100 has a license key in Step 420, the validity check module 174 determines whether the license key of the user terminal 100 is valid in Step 430.

When determining the validity in Step 430, the validity check module 174 uses the Dev ID 160, the App ID 171, and the code book 175. The method for determining validity of a license key using the Dev ID 160, the App ID 171, and the code book 175 will be explained later in detail.

If it is determined that a license key is valid in Step 430, the DRM client 172 allows the application 170 to be executed, and thus the controller 130 executes the application 170 in Step 440.

If it is determined that the user terminal 100 does not have a license key in Step 420, or if it is determined that the user terminal 100 has an invalid license key in Steps 420 and 430, the DRM client 172 does not allow the application 170 to be executed, and thus the controller 130 may not execute the application 170 in Step 450.

Instead, the license agent module 173 displays a message for inquiring whether to issue a license key through the user interface 120 in Step 460 in order to induce a user to receive a valid license key from the application providing server 200. The user viewing the message displayed in Step 460 may request a license key to be issued using the user interface 120.

If the command to request a license key to be issued is input in Step 470, the license agent module 173 requests the application providing server 200 to issue a license key in Step 480. The message for inquiring whether to issue a license key in Step 480 includes the Dev ID 160 and the App ID 171. If the application providing server 200 issues a license key in response to the request in Step 480 in Step 490, the license agent module 173 stores the issued license key in the storage unit 140, and then Step 420 is re-performed.

However, if the license agent module 173 requests the application providing server 200 to issue a license key in Step 480, and the application providing server 200 does not issue a license key in Step 490, the process ends and the application is not executed.

The license key process where the license agent module 173 requests the application providing server 200 to issue a license key in Step 480, and thus the application providing server 200 issues a license key to the user terminal 100 is described with reference to FIG. 5.

As illustrated in FIG. 5, if the application providing server 200 receives the request for issuing a license key in Step 510, the validity check module 251 of the DRM server 250 executed by the controller 220 of the application providing server 200 determines whether the received request for issuing a license key is proper in Step 520.

The determination in Step 520 is for determining whether a proper module to issue a license key, that is whether the license agent module 173 of the DRM client 172 packed in the application 170 generates the request for issuing a license key.

If it is determined that the request for issuing a license key is proper in Step 520, the purchase confirmation module 252 of the DRM server 250 identifies whether the user terminal 100 has a history of purchasing the application 170 in Step 530.

As described above, the request for issuing a license key received in Step 510 comprises the Dev ID 160 and the App ID 171. In the DB of purchase list 260, Dev ID of a user terminal which purchases application is mapped one to one to App ID of application which the user terminal purchases.

In Step 530, the purchase confirmation module 252 may identify whether there is a history of purchasing the application by determining whether the Dev ID 160 and the App ID 171 included in the request for issuing a license key received in Step 510 are mapped one to one with the DB of purchase list 260.

If it is determined that the user terminal 100 has a history of purchasing the application 170 in Step 530, the license key generation module 253 generates a license key in Step 540.

The license key generation module 253 transmits the license key generated in Step 540 to the license agent module 173 of the DRM client 172 in Step 550.

The method for generating the license key where the license key generation module 253 generates a license key is described with reference to FIG. 6. FIG. 6 is a diagram illustrating a method for generating a license key according to an embodiment of the present invention.

As shown in FIG. 6, the license key generation module 253 may generate a license key by applying a hash function to the Dev ID 160, the App ID 171, and a text stream retrieved from the code book 254.

Herein, the text stream retrieved from the code book 254 is generated in a manner of extracting part of the texts contained in the code book 254.

FIG. 7 is a diagram illustrating a method for generating a text stream according to an embodiment of the present invention. Referring to FIG. 7, texts contained in the large box correspond to the texts contained in the code book 254, and the texts contained inside the small box correspond to the extracted texts. As shown in FIG. 7, the text stream is a part extracted from the code book 254.

The part which is extracted from the code book 254 to be a text stream is decided by the Dev ID 160 and the App ID 171. The license key generation module 253 decides part which will be extracted from the code book 254 to be a text stream using the Dev ID 160 and the App ID 171.

For example, the license key generation module 253 extracts a text stream having letters from $m^{th}$ to $n^{th}$ from the code book 254. Herein, m and n may be calculated by the following relation.

$$m:\text{(the number of letters in the Dev ID 160×the number of letters in the App ID 171×1,000,000)\% 777}$$

that is, m is the remainder of dividing the multiplication of the number of letters in the Dev ID 160, the number of letters in the App ID 171, and 1,000,000 by 777

$$n:\text{(the number of letters in the Dev ID 160×the number of letters in the App ID 171×1,000,000)\% 999}$$

that is, n is the remainder of dividing the multiplication of the number of letters in the Dev ID 160, the number of letters in the App ID 171, and 1,000,000 by 999

Alternatively, the license key generation module 253 extracts a text stream having n letters from $m^{th}$ from the code book 254. Herein, m and n may be calculated by the above relation. By doing so, the length of a text stream may be kept constant "n."

The generated license key is transmitted to the user terminal 100, and the storage unit 140 stores the license key.

Determining whether a license key stored in the user terminal 100 is valid in Step 430, the validity check module 174 generates a license key using the Dev ID 160, the App ID 171, and the code book 175. Herein, the license key is generated in the same manner as that of FIG. 6.

The validity check module 174 compares the generated license key with the license key stored in the user terminal 100 in order to determine whether they are the same. If the generated license key and the license key stored in the user terminal 100 are the same, the validity check module 174 determines that the license key stored in the user terminal 100 is valid.

However, if the generated license key is different from the license key stored in the user terminal 100, the validity check module 174 determines that the license key stored in the user terminal 100 is invalid because, the license keys are not the same if the license key in the user terminal 100 has been issued improperly.

As described above, according to the embodiments of the present invention, an application is executed only on the device which has purchased the application or the device which has a legal right, and illegal use of applications is prevented.

While the present invention has been shown and described with reference to various embodiments thereof, the present invention can be readily applied to other types of apparatuses. The description of the various embodiments of the present invention is intended to be illustrative, and it will be apparent to those of ordinary skill in the art that various changes in form and detail can be made without departing from the spirit or scope of the present invention, defined by the appended claims.

The invention claimed is:

1. An application protection method, comprising:
   providing a user terminal with an application;
   generating a key needed to execute the application using information on the user terminal, information on the application, and a part of text extracted from a code book; and
   transmitting the generated key to the user terminal,
   wherein the part of text extracted from the code book is decided based on the information on the user terminal and the information on the application, and
   wherein the part of text is a text string having letters starting from an $m^{th}$ letter and ending at an $n^{th}$ letter in the code book and wherein m and n are numbers calculated using the information on the user terminal and the information on the application.

2. The application protection method as claimed in claim 1, wherein generating the key applies a hash function to the information on the user terminal, the information on the application, and the part of text, and generates the key.

3. The application protection method as claimed in claim 1, wherein the information on the user terminal comprises identification (ID) of the user terminal, and the information on the application comprises identification (ID) of the application.

4. The application protection method as claimed in claim 1, wherein
   generating the key is performed when it is determined that the user terminal has purchased the application.

5. The application protection method as claimed in claim 1, wherein the code book is stored in a server.

6. The application protection method as claimed in claim 5, wherein the code book stored in the sever is identical to a code book included in the application.

7. An application execution method, performed by a user terminal, comprising:
   determining whether a key which is generated to execute an application using information on the user terminal, information on the application, and a part of text extracted from a code book is valid; and
   executing the application if it is determined that the key is valid,
   wherein the part of text extracted from the code book is decided based on the information on the user terminal and the information on the application, and
   wherein the part of text is a text string having letters starting from an $m^{th}$ letter and ending at an $n^{th}$ letter in the code book, and wherein m and n are numbers calculated using the information on the user terminal and the information on the application.

8. The application execution method as claimed in claim 7, wherein determining and executing the application are performed by a Digital Rights Management (DRM) program which is packed in the application.

9. The application execution method as claimed in claim 7, wherein the valid key is generated by applying a hash function to the information on the user terminal, the information on the application, and the part of text.

10. The application execution method as claimed in claim 7, wherein the information on the user terminal comprises identification of the user terminal, and the information on the application comprises identification of the application.

11. The application execution method as claimed in claim 7, further comprising:
    determining whether a key needed to execute the application is stored;
    requesting the key when it is determined the key needed to execute the application is not stored; and
    receiving and storing the key in response to the request.

12. The application execution method as claimed in claim 11, wherein receiving and storing the key is performed when the user terminal has purchased the application.

13. The application execution method as claimed in claim 7, wherein determining whether the key is valid comprises comparing the key generated in the application with a key generated in a server.

14. An application protection method, comprising:
    providing a user terminal with an application;
    generating a key needed to execute the application using information on the user terminal, information on the application, and a part of text extracted from a code book; and
    transmitting the generated key to the user terminal,
    wherein the part of text extracted from the code book is decided based on the information on the user terminal and the information on the application, and
    wherein the part of text is a text string having n letters starting from an $m^{th}$ letter in the code book, and wherein m and n are numbers calculated using the information on the user terminal and the information on the application.

15. An application execution method, performed by a user terminal, comprising:
    determining whether a key which is generated to execute an application using information on the user terminal, information on the application, and a part of text extracted from a code book is valid; and
    executing the application if it is determined that the key is valid,
    wherein the part of text extracted from the code book is decided based on the information on the user terminal and the information on the application, and
    wherein the part of text is a text string having n letters starting from an $m^{th}$ letter in the code book, and wherein m and n are numbers calculated using the information on the user terminal and the information on the application.

* * * * *